Figure 1:
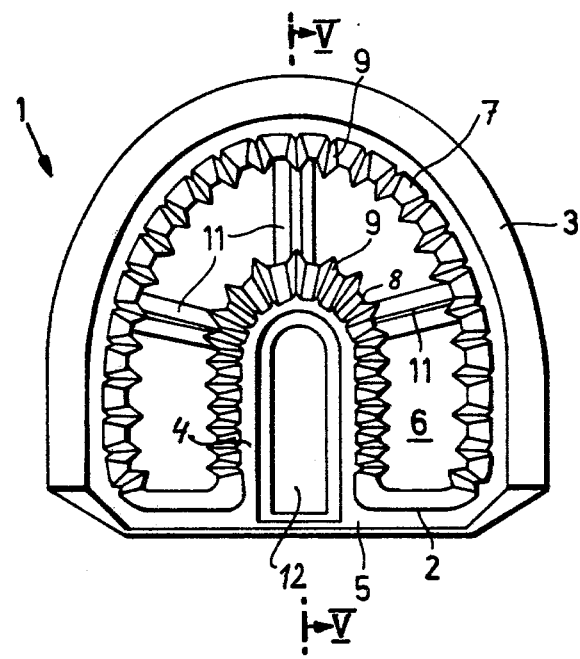

United States Patent [19]

Browne et al.

[11] 4,283,173
[45] Aug. 11, 1981

[54] DEVICE FOR THE PRODUCTION OF A DENTAL WORKING MODEL FOR THE PREPARATION OF PROSTHETIC WORKS

[75] Inventors: Laurence S. Browne, Godalming, England; Frank D. Braun; Walter Witt, both of Cologne, Fed. Rep. of Germany

[73] Assignee: Jet-Ceramic Dental GmbH & Co. KG, Cologne, Fed. Rep. of Germany

[21] Appl. No.: 24,862

[22] PCT Filed: Jul. 26, 1978

[86] PCT No.: PCT/DE78/00015

§ 371 Date: Apr. 1, 1979

§ 102(e) Date: Mar. 28, 1979

[87] PCT Pub. No.: WO79/00076

PCT Pub. Date: Feb. 22, 1979

[30] Foreign Application Priority Data

Aug. 1, 1977 [GB] United Kingdom ............... 32133/77

[51] Int. Cl.³ .............................................. A61C 19/00
[52] U.S. Cl. ....................................... 433/34; 249/54; 425/179
[58] Field of Search ...................... 433/34, 196, 36, 37, 433/49; 249/54, 155; 425/175, 176, 179

[56] References Cited

U.S. PATENT DOCUMENTS

| 2,058,838 | 10/1936 | Stahl | 249/54 |
| 2,577,420 | 12/1951 | Jablonski et al. | 433/34 |
| 2,786,272 | 3/1957 | Lindley | 433/196 |
| 3,128,725 | 4/1964 | Becker et al. | 249/155 |
| 3,686,759 | 8/1972 | Pross geb. Hogreve | 433/37 |
| 3,702,027 | 11/1972 | Marshall et al. | 433/34 |
| 3,882,601 | 5/1975 | Jahn | 433/214 |
| 4,022,419 | 5/1977 | Haker | 249/54 |
| 4,059,902 | 11/1977 | Shiokawa | 433/34 |
| 4,116,416 | 9/1978 | Segura | 433/34 |

Primary Examiner—Gene Mancene
Assistant Examiner—John J. Wilson
Attorney, Agent, or Firm—Friedman, Goodman & Teitelbaum

[57] ABSTRACT

The invention relates to a device for producing a working model for making dental prostheses, which comprises a base presenting an open portion on both sides and features a hollow portion adapted to the shape of the jaws and presenting ribs on both inner surfaces, said ribs acting as retaining members for the plaster model and having the shape of ramps with a constant slope from top to bottom, the hollow portion widening from bottom to top. Between the inner wall of the base and its back wall is a horizontal plate which has roughly the shape of a parabola, said horizontal plate being set off downwards and with respect to the top edge of the wall.

12 Claims, 9 Drawing Figures

DEVICE FOR THE PRODUCTION OF A DENTAL WORKING MODEL FOR THE PREPARATION OF PROSTHETIC WORKS

The present invention concerns a device for the production of a dental working model for the preparation of prosthetic works.

There is already known a method for the production of tooth crowns and tooth bridges, in which a casting mould is employed as model base, which consists of three individual assemblable parts, and namely an about mandible-shaped base plate with a step, starting from the straight rear side of the base plate and approximately adapted to the shape of the tongue, as well as an outside wall adapted to the shape of the base plate and with a rear wall and vertical grooves provided at its inside. The assembled mould is plaster-filled and the likewise plaster-filled correction imprint is laid on this, plaster side on plaster side. After the hardening, the thus produced plaster model can be removed by detachment of the individual parts of the casting mould and subsequently be sawn through between the individual tooth stumps. Through the grooves of the outside wall, ribs are developed at the plaster model, which shall guarantee a firm seat of the sawn model parts in the model base. This model base used as casting mould is however entailed by the disadvantages that it is not sufficiently rigid so that the individual parts do not sit absolutely immovably in the base, but in part resiliently after the sawing apart of the plaster model. Moreover, the individual parts can be taken out or put in only after the detaching of the outside wall, whereby a redisposition of the remaining individual parts can result. Furthermore, the plaster model is only inadequately guided in the base. All these disadvantageous properties altogether lead thereto, that inaccuracies at the plaster model can arise in the modelling of the crown or the bridge and altogether let the known process appear to be unsuitable.

The invention is now based on the task, proceeding from the afore-described state of the art, to improve this in such a manner that a rigid, absolutely secure and exact guidance of the plaster model, especially in the sawn-through state takes place in the model base and an easy removing of the plaster model from the mould is possible. According to the invention, this is attained through a model base, which is characterised thereby, that it consists of a one-part base mould with a hollow space adapted to the size of the mandible with ribs developed at both its equally high inside surfaces for the development of retention marks. It is in that case particularly expedient when the hollow space enlarges in about frustoconical shape upwardly from below and the ribs are developed in the shape of ramps and wedge-shaped in cross-section and rise steadily from the upper to the lower rim of the hollow space. It is furthermore of advantage when the rib edge is rounded off. It is in that case provided according to the invention that the hollow space is open upwardly and downwardly. Through this structuring according to the invention, especially the conical shaping of the hollow space, the ramp-shaped structuring of the ribs and the rounded-off rib edges, there results an easy removal from the mould of the hardened plaster model from the model base, and namely without any kind of mechanical aids being necessary for this, but this removal from the mould can take place through light pressure from below against the mass of plaster, because the hollow space is also open downwardly. Furthermore, the downwardly open construction of the hollow space possesses the advantage that it can be checked accurately whether the entire hollow space has been completely filled during the casting and especially whether the plaster material has distributed itself uniformly in the rib interstices so that the later hardened plaster model with the positive imprint of the teeth or tooth stumps applied above displays retention grooves shaped by the ribs of the model base in its lower guide region sitting in the model base. The presence of retention grooves to both sides of the plaster model assures an absolutely secure both-sided guidance of the stumps in the model base particularly after the sawing apart of the plaster model. In that case, a guidance of the individual parts takes place independently of one another so that these can be drawn out or inserted as desired without a redisposition of the neighbouring individual parts in the model base having to be feared. The number of the ribs present at both inside walls of the hollow space is in principle as desired. However, it is particularly advantageous to provide as many ribs as possible, and namely equally many at both walls in order to possess as great as possible a number of retention marks in the plaster model so that a secure retention of the sawn-apart stumps in the plaster model is assured in any case.

For the additional stiffening of the in itself already rigidly developed model base, webs are according to the invention developed in the lower part of the hollow space between both the walls of the same. Advantageously, three webs are present, which are flattened off downwardly so that a planar support surface of the model base results.

Expediently, the model base possesses a height of about 2 to 3 centimeters, i.e. if possible 2 to 3 times the height of the teeth, onto which in the plaster-filled state, the imprint is placed plaster surface onto plaster surface, because thereby an adequately long quidance region of the finished positive imprint body in the model base results, which is of importance particularly after the sawing-apart of the body into the individual parts. A relatively short guidance region would lead thereto, that an not adequately firm seat of the individual stump would be present and would make more difficult the later dental processing.

For the remainder, it must be pointed out that only the conical, upwardly opening execution of the hollow space provided according to the invention makes it possible to keep the hollow space open downwardly, since a natural limitation of the plug-in path of the sawn-apart individual parts takes place through this conical form of execution, so that these cannot fall through downwardly.

Figure 2:
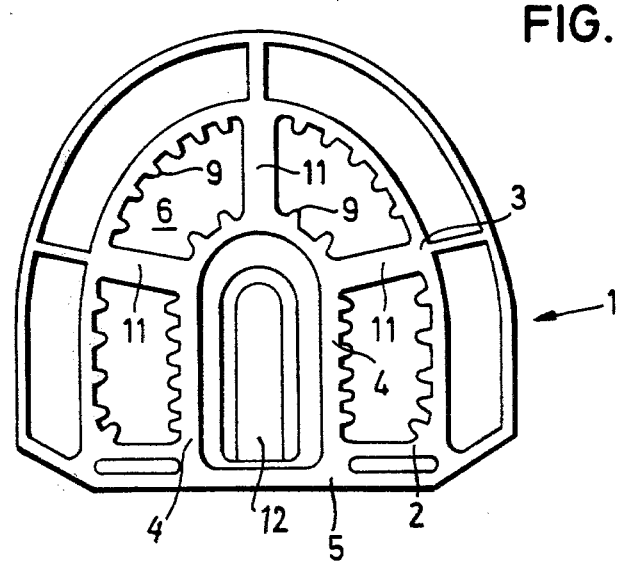
Figure 3:
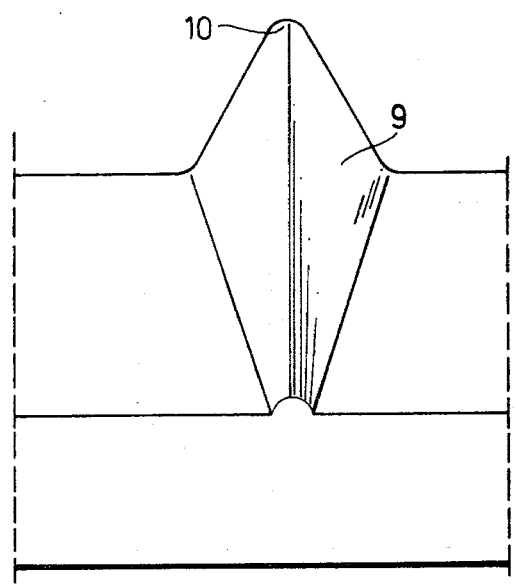
Figure 6:
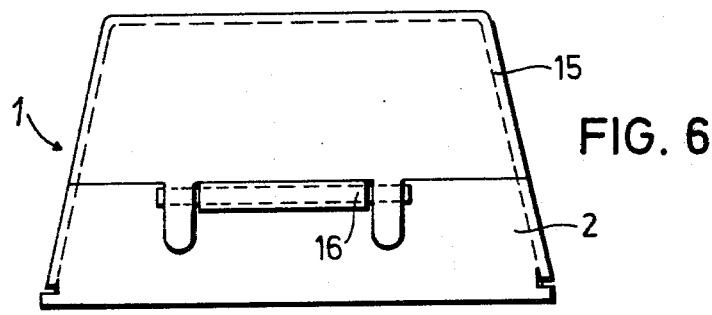
Figure 7:
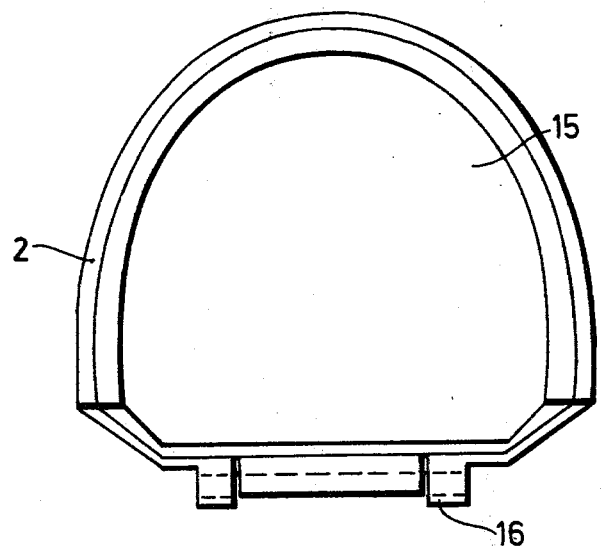
Figure 8:
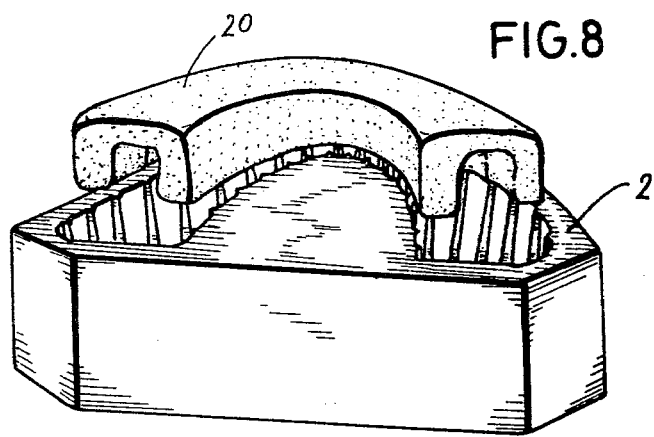
Figure 9:
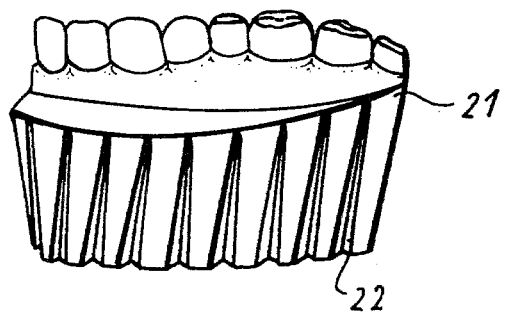

The invention is more closely explained by reference to the example of embodiment illustrated in the accompanying drawings. There show:

FIG. 1 a view from above onto a base mould according to the invention,

FIG. 2 a view from below onto a base mould according to the invention and FIG. 1, FIG. 3 a detail of the base mould according to FIG. 1, FIG. 4 a perspective view, partly sectioned of the base mould according to the invention and FIG. 1, FIG. 5 a section along the section line V—V in FIG. 1 with simultaneous showing of an insert usable according to the invention, FIG. 6 a side view of the rear side of the base mould according to the invention with lid, FIG. 7 a view onto the base mould according to FIG. 6, FIG. 8 a view of a base mould according to the invention with correction imprint body placed on, and FIG. 9 a view of a positive imprint body produced with the aid of the base mould according to the invention.

Figure 4:
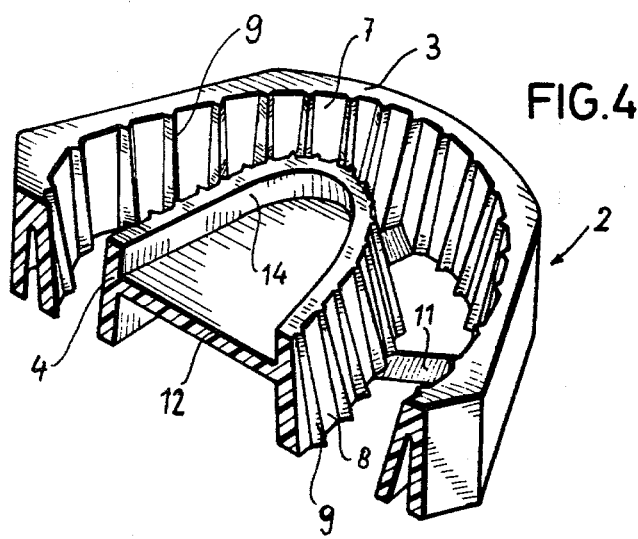

As is illustrated in the FIGS. 1 and 2 and 4, a base mould 1 according to the invention, which serves as prefabricated part as model base of a working model or sawing model for the setting-up of prosthetic works, consists of a mould body 2 adapted to the mandible sizes. This mould body is developed as rigid synthetic material part resistant to deformation. Suitable as synthetic material is a synthetic material of polycarbonic acid ester of the 4,4-dioxide phenyl-2,2-propane (polycarbonate), which is very temperature-resistant, acid-resistant and dimensionally stable. The further advantage of this synthetic material consists therein, that it is transparent and as clear as glass. This mould body 2 displays a semicircularly shaped outside wall 3, which displays a middle rounded-off and two oppositely disposed, laterally flattened-off parts and an inner about parabolically shaped wall 4 as well as a rear wall 5, which closes off the mould body at the rear side. Formed by these walls 3, 4 and 5 is a hollow space 6, which about corresponds to the shape of the mandible and which enlarges upwardly from below so that it possesses an about frustoconical profile in cross-section. Small ribs 9 are developed at the inside surfaces 7 and 8 of the hollow space. In that case, a largest possible number of ribs 9 is present, preferably about 15 to 30 ribs being distributed beside one another at the inside surface. The number of the ribs 9 should preferably be equally great at both inside surfaces 7 and 8. The spacings of the ribs 9 among one another become closer towards the middle of the inside surfaces. The profile of the ribs is about ramp-shaped, beginning at the upper edge of the hollow space 6 and rising continuously towards the lower edge, while the final height of the ramp amounts to about 2 to 3 millimeters. The wall height of the mould body amounts to about 2 to 3 centimeters. The hollow space 6 is open downwardly, however bottom webs 11 being developed in its lower region and connecting both the walls 3 and 4 and serving as spacer members and for stiffening. Developed between the rear wall 5 and the outside surface of the inner wall 4 is a horizontal plate 12, which extends displaced downwardly relative to the upper edges of the walls 4 and 5. Thereby results an upwardly open space 13, which is separated from the hollow space 6 by a web 14. In a simplified form, the plate 12 can also close off flush with the upper edges of the walls 4 and 5. The mould body 2 is closable from above by a lid 15, which is connected with the mould body 2 through a joint 16. The lid expediently consists likewise of the same material as the mould body.

The function of the base mould according to the invention is as following. After an imprint has been produced by the dentist, in which the prepared teeth as well as also the gum and mandible portions have been imprinted according to need, this imprint which represents the negative is filled by a special plaster mass in the laboratory or in the dental practice. At the same time, the mould body of the base mould 1 is filled in its hollow space 6 completely up to the edge with the same mass or for saving in costs with a mass of lesser quality, for which the base mould 1 is placed on a planar support. Due to the execution of the base mould 1 open from the under-side and transparent from all sides, it can be checked whether the cast mass has distributed itself uniformly over the entire hollow space and has also penetrated uniformly into all rib interstices. The imprint is now in the still plastic state of the cast masses laid with its plaster side onto the base mould 1, and namely on the plaster side thereof, as this is illustrated in FIG. 8. Thereby, the cast masses disposed in both the parts can connect with each other. After the hardening, the cast mass carrier 20 can be taken off and the arisen working model is placed ready. In that case, the working model comprises on the one hand the prefabricated base mould 1 and on the other hand the positive imprint body 21, which is disposed in the base mould 1 and as it is illustrated in FIG. 9. This positive imprint body 21 in its upper region displays the teeth, the course of the gums and the palate and in the lower region a guide section which displays retentions 22, which have developed during the casting process through the ribs 9 of the mould body 2. The removal from the mould of the positive imprint body 21 out of the base mould 1 can take place easily and without difficulties, which is made possible substantially through the frustoconical cross-sectional profile of the hollow space 6 and the ramp-shaped development of the ribs 9. Beyond that, the employed manufacturing material of the base has the property that no connection is entered into between the cast mass and the base so that an otherwise necessary insulation can be dispensed with.

By reason of the height of the moulded body and the height resulting therefrom of the lower guidance region of the positive imprint body, a secure guidance of the same take place in the base mould. For further processing, only the positive imprint body can be subdivided into individual parts by sawing in any desired technique. By reason of the long guidance section and the ribs disposed at both walls 3 and 4 in the base mould and the corresponding retentions in the individual parts arisen through sawing, an exact positioning of the same is possible in the base mould which serves as model base. In that case, an absolutely rigid seating is attained so that an absolutely precise working model stands at disposal for the preparation of a crown or bridge.

Figure 5:
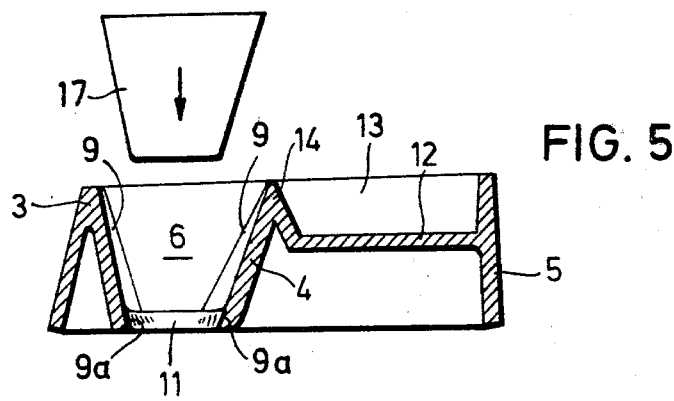

As is evident from FIG. 5, an insert 17 can be inserted from above into the hollow space 6 of the mould body 2, whereby the hollow space can be subdivided. A subdivision of that kind is to be recommended when only partial imprints are to be produced. In that case, the insert 17 is structured in such a manner that it can be pushed in between the ribs 9 so that a firm and tight seating is generated.

In the production of upper mandible imprints, also the palate must be impressed in many cases. For this reason, the mould body according to the invention possesses the space 13, which is normally separated from the hollow space 6 by the web 14. For the case that the palate is also to be cast, the web is milled away when necessary so that the hollow space 6 and the space 13 stand in connection with each other and together can be filled by a cast mass so that now the impression with the palate imprint section can likewise be placed on. The hollow space underneath the plate 12 is suitable for the fastening of any kind of articulators.

In that a lid is additionally fastened at the mould body, a protection results against external influences and a packaging ready for dispatch. Through the use of the base mould according to the invention, it is possible for the dentist to produce the working model directly in his practice in simple and rapid manner, while a high accuracy is assured. Thereby, the costs connected with the production of tooth bridges are also appreciably reduced through the use of the base mould according to the invention, since the arising labour effort is considerably lessened. In addition, the base moulds according to the invention can be used several times. Moreover, inaccuracies are largely excluded, since an absolute accuracy to size of the sawn tooth stumps within the base mould is assured through the retentions present at both sides due to the use of the prefabricated rigid mould body. Beyond that, a long guidance region is generated within the base mould so that a wobblefree seating is present. The base mould according to the invention makes it possible with a sawing technique, in which the individual stumps are sawn into from below and above displaced laterally to each other, to locate the entire sawn plaster body in the model base through arresting of a certain individual stump. This arresting can take place through a lateral insertion of a pin through the correspondingly drilled outside wall of the model base in the respective drilled individual stump or a corresponding segment.

We claim:

1. Device for production of a dental working model for preparation of a prosthetic work comprising:
   a one-part base mould which functions as a model base;
   said base mould including a substantially semicircularly shaped outside wall spaced from a substantially parabolically shaped inner wall, and a rear wall connecting said inner and outside walls for closing off a rear side of said base mould;
   said outside, inner and rear walls providing a hollow space which is completely surrounded by said outside, inner and rear walls;
   said hollow space enlarging upwardly from a bottom of said base mould to a top of said base mould;
   said hollow space including first opening means through said base mould bottom and also including second opening means through said base mould top to provide an open elongated passageway through said base mould, said first and second opening means extending substantially along a major longitudinal length of said hollow space from one portion of said rear wall on one side of said base mould to an opposing portion of said rear wall on an opposite side of said base mold to define said open elongated passageway for permitting removal of a casted plaster model from said hollow space of said base mould;
   rib means disposed on facing wall surfaces of said hollow space for providing retention marks on the plaster model, said rib means including ribs extending outwardly from said outside and inner walls into said hollow space; and
   said outside and inner walls being of equal height with each of said ribs having a length equal to said height so that said ribs extend from within said first opening means of said base mould bottom to within said second opening means of said base mould top.

2. Device according to claim 1, wherein an outer edge of each of said ribs is rounded.

3. Device according to claim 1, wherein lower portions of said outside and inner walls are connected together by at least one web extending across said hollow space.

4. Device according to claim 1, wherein a substantially parabolia horizontal plate is surrounded by said inner wall and said rear wall.

5. Device according to claim 4, wherein said horizontal plate is downwardly spaced from said base mould top.

6. Device according to claim 1, including at least one insert which is insertable into said hollow space for subdividing said hollow space.

7. Device according to claim 1, including a cover which is articulately fastened to said base mould to cover said base mould from above.

8. Device according to claim 1, wherein said base mould has a height which amounts to at least two to three times a height of a correction imprint put on.

9. Device according to claim 1, wherein 15 to 30 ribs extend outwardly from said outside and inner walls into said hollow space.

10. Device according to claim 1, wherein said base mould is fabricated from a rigid synthetic material.

11. Device according to claim 1, wherein said base mould is fabricated from metal.

12. Device for production of a dental working model for preparation of a prosthetic work comprising:
    a one-part base mould which functions as a model base;
    said base mould including a substantially semicircularly shaped outside wall spaced from a substantially parabolically shaped inner wall, and a rear wall connecting said inner and outside walls for closing off a rear side of said base mould;
    said outside, inner and rear walls providing a hollow space which is completely surrounded by said outside, inner and rear walls;
    said hollow space enlarging upwardly from a bottom of said base mould to a top of said base mould;
    said hollow space being open at said base mould bottom and also being open at said base mould top to provide an opening through said base mould to permit removal of a casted plaster model from said hollow space of said base mould;
    rib means disposed on facing wall surfaces of said hollow space for providing retention marks on the plaster model, said rib means including ribs extending outwardly from said outside and inner walls into said hollow space;
    said outside and inner walls being of equal height with each of said ribs having a length equal to said height so that said ribs extend from said base mould bottom to said base mould top; and
    each of said ribs having a ramp shape with a constant slope from said base mould top to said base mould bottom so that each of said ribs has its greatest height at said base mould bottom, each of said ribs being wedge-shaped in cross-section.

* * * * *